United States Patent [19]

Atadan et al.

[11] Patent Number: 5,292,944
[45] Date of Patent: Mar. 8, 1994

[54] PROCESS FOR THE PREPARATION OF ADIPIC ACID OR PENTENOIC ACID

[75] Inventors: Erdem M. Atadan, Wilmington; Harold S. Bruner, Jr., Hockessin, both of Del.

[73] Assignee: E. I. Du Pont de Nemours and Company, Wilmington, Del.

[21] Appl. No.: 81,885

[22] Filed: Jun. 29, 1993

[51] Int. Cl.$^5$ .................... C07C 51/12; C07C 51/10
[52] U.S. Cl. .................... 562/590; 562/517; 562/522
[58] Field of Search ............... 562/590, 591, 517, 522

[56] References Cited

U.S. PATENT DOCUMENTS

| | | |
|---|---|---|
| 3,579,551 | 5/1971 | Craddock et al. ............ 562/522 X |
| 3,816,489 | 6/1974 | Craddock et al. ............ 562/522 |
| 4,334,092 | 6/1982 | Knifton ............ 562/517 |
| 4,612,387 | 9/1986 | Feitler ............ 560/232 |
| 4,622,423 | 11/1986 | Burke ............ 562/522 |
| 4,640,802 | 2/1987 | Drent ............ 260/410.9 R |
| 4,659,518 | 4/1987 | Rizkalla ............ 260/413 |
| 4,780,334 | 10/1988 | Burke ............ 427/248.1 |
| 4,788,333 | 11/1988 | Burke ............ 562/517 |
| 4,939,298 | 7/1990 | Burke ............ 562/591 |

*Primary Examiner*—Arthur C. Prescott

[57] ABSTRACT

Six carbon diacids or lactones or 5 carbon lactones or 6 carbon diacid anhydrides or branched mono-olefinic five carbon acids are converted (isomerized) to adipic acid or pentenoic acids by reacting them is the presence of carbon monoxide and a iodide promoted iridium catalyst.

7 Claims, No Drawings

PROCESS FOR THE PREPARATION OF ADIPIC ACID OR PENTENOIC ACID

FIELD OF THE INVENTION

This invention relates to the preparation of adipic acid and/or pentenoic acid. These acids are prepared by isomerization or dehydrocarboxylation of a commercially less-desirable compound. In particular this invention relates to the conversion of a by-product stream (from the preparation of adipic acid from pentenoic acid by carbonylation using a rhodium or an iridium catalyst promoted with a halide) to adipic acid or to pentenoic acid.

BACKGROUND OF THE INVENTION

The dominant commercial process for the manufacture of adipic acid involves the air-oxidation of cyclohexane to form a mixture of cyclohexanol and cyclohexanone, which is subsequently oxidized with nitric acid to form a mixture of carboxylic acids, including adipic acid.

Another process for making adipic acid involves the hydrocarboxylation of pentenoic acids and their esters. Pentenoic acids and their esters, and in particular 3-pentenoic acid, are available from butadiene and butadiene derived feedstocks by metal catalyzed hydrocarboxylation. Such processes have the potential of providing high yield, high rate, low pollution processes for the manufacture of adipic acid. In the hydrocarboxylation of 3-pentenoic acid and its esters, higher levels of branched products are formed than are normally encountered in the hydrocarboxylation of simple olefins. Burke (U.S. Pat. No. 4,788,333) has disclosed that, for the production of adipic acid by the hydrocarboxylation of pentenoic acids, high linear selectivity is obtained when an iodide-promoted rhodium catalyst is employed in conjunction with selected halocarbon solvents.

Burke discloses in U.S. Pat. No. 4,939,298, the branched diacids can be separated from the product adipic acid and then isomerized to adipic acid by heating in the presence of carbon monoxide and an iodide or bromide promoted rhodium catalyst.

The most commonly used promoters for metal catalyzed hydrocarboxylation also promote the conversion of pentenoic acids and esters to gamma-valerolactone. This material can also be separated from the product adipic acid and hydrocarboxylated to adipic acid as described in Burke EPO published application 90107900.4, but there are costs and yield losses associated with such processes.

Craddock et al (U.S. Pat. No. 3,816,489) disclose a process "for the production of terminal carboxylic acids" from "ethylenically unsaturated compounds" by hydrocarboxylation "in the presence of catalyst compositions essentially comprising iridium compounds and complexes, together with an iodide promoter in critical proportions". In U.S. Pat. No. 3,816,488 Craddock et al disclose that similar results can be obtained using rhodium catalysts. The preferred reaction solvents are monocarboxylic acids having 2 to 20 carbon atoms.

European Patent Application No. 0 511 126 A2 published Oct. 28, 1992 discloses the preparation of adipic acid by hydrocarboxylation of pentenoic acid using an iridium catalyst promoted with an iodide.

U.S. Pat. No. 3,090,807 (Illing et al.) discloses a process for the isomerization of aliphatic carboxylic acids by heating with carbon monoxide "in the presence of (a) a metal carbonyl and (b) chlorine, bromine, or iodide and/or one or more compounds of one or more of these halogens as catalysts, and preferably in the presence of (c) an activator and (d) water." Suitable metal carbonyls are those of the 6th, 7th and 8th group of the periodic system. Metal carbonyls of the iron group, especially cobalt and nickel, are preferred. The most preferred is nickel. The isomerization of adipic acid to 2-methylglutaric acid and 2,3-dimethylsuccinic acid is discussed and exemplified in Examples 1 and 6. In Example 1 nickel carbonyl activated by bismuth iodide is employed while in Example 6 cobalt acetate activated by bismuth oxide and hydrogen iodide is employed. Although the process is said to be suitable for the isomerization of linear acids to branched acids and branched acids to linear acids, there is no mention of the isomerization of branched C6-diacids to adipic acid.

Taiwan Patent 047769 to Burke discloses a process for the preparation of adipic acid by the carbonylation of certain lactones including gamma-valerolactone in the presence of a rhodium catalyst and an iodide or bromide promoter.

U.S. Pat. No. 3,625,996 (Union Oil) discloses a process for the preparation of olefinic acids or esters from diacids or esters by contacting with a complex catalyst comprising a Group VIII noble metal and a ligand from the group consisting of organic phosphines, arsines and stiblines. Iridium is mentioned as a catalyst.

U.S. Pat. No. 3,592,849 (Union Oil) discloses a process for the "preparation of acids from their anhydrides with isomerization of the acid by contacting the anhydride with a catalyst comprising a complex of a Group VIII metal and a biphyllic ligand" at elevated temperature. The process produces carboxylic acid, olefin and CO. The biphyllic ligands are selected from organic compounds containing arsenic, antimony, phosphorus or bismuth in a trivalent state. Iridium is mentioned as a group VIII metal that may be employed.

U.S. Pat. No. 5,077,447 (Henkel) discloses a process for making olefins by reaction of a mixture of carboxylic acid and a carboxylic anhydride in the presence of a Group VIII metal or copper containing catalyst. Iridium is mentioned as a group VIII metal that may be employed. In Example 8, an iridium catalyst is employed to convert decanoic acid to 1-nonene.

SUMMARY OF THE INVENTION

The present invention is a process for the preparation of adipic acid and/or pentenoic acids which comprises (1) forming a reaction mixture containing (a) one or more acids or lactones selected from saturated branched six carbon diacids, saturated five carbon lactones, saturated six carbon diacid anhydrides and branched mono-olefinic five carbon monoacids (b) carbon monoxide, and (c) a iodide promoted iridium catalyst (2) heating said reaction mixture to a temperature in the range of about 175 degrees C. to about 230 degrees C. while under a carbon monoxide pressure of between 0 to 2000 psi absolute and where the ratio of active iodide to iridium in the reaction mixture is 0.5:1 to 20:1, and the iridium content of the reaction mixture is about 100 to 8,000 parts per million by weight of the reaction mixture. If the process is carried out toward the lower end of the carbon monoxide pressure range (0 to 10 psi absolute) most of the product will be pentenoic acid. If the process is carried out toward the upper end of the carbon monoxide pressure range (200 to 2000 psi absolute) most of the product will be adipic acid. Usual constituents in the mixture to be reacted include gamma-valerolactone, 2-methylglutaric acid, 2-ethylsuccinic acid, and 2,3-dimethylsuccinic acid.

DETAILED DESCRIPTION

When pentenoic acid is hydrocarboxylated using a rhodium or iridium catalyst promoted with halide, adipic acid is formed, but also other compounds including gamma-valerolactone, 2-methylglutaric acid, 2-ethylsuccinic acid, and 2,3-dimethylsuccinic acid. Depending on the conditions employed for the hydrocarboxylation, these mixtures may also contain cyclic or linear anhydrides derived from carboxylic acid solvents, starting materials or products. Examples of cyclic anhydrides which may be present include 2-ethylsuccinic anhydride and 2,3-dimethylsuccinic anhydride. Linear anhydrides include symmetrical anhydrides as well as mixed anhydrides. Adipic acid may be separated from this mixture by crystallization. The mixture of by-products is then treated in accordance with the present invention. Branched C6-diacids are isomerized to adipic acid or dehydrocarboxylated to pentenoic acid. C5-Lactones are hydrocarboxylated to adipic acid and branched C6-diacids or isomerized to pentenoic acid. The pentenoic acid can then be reacted with carbon monoxide to form adipic acid.

The gamma-valerolactone or alpha-methyl-gamma-butyrolactone used as the starting materials for the process of this invention may be obtained from the hydrocarboxylation reaction described in U.S. Pat. No. 4,788,333, or they may be obtained from any other source. The synthesis of alpha, beta-dimethylpropiolactone, alpha-ethylpropiolactone and beta-ethylpropiolactone has been described in the prior art.

The iridium catalyst can be derived from any iridium compound or mixture of iridium compounds that is free of interfering ligands, such as bidentate phosphines and nitrogen ligands, and that is capable of forming a homogeneous solution under the reaction conditions. Suitable iridium compounds include those described in U.S. Pat. No. 3,816,489 to Craddock et al. The amount of iridium in the reaction mixture should be in the range of 50 to 7000 ppm by weight and preferably in the range of 500 to 2000 ppm. The weight of the reaction medium includes the weight of solvent, catalyst, promoter, and reactants.

The catalyst, which can be performed or can be formed in situ, must be promoted to achieve a satisfactory reaction rate. Suitable promoters are iodide compounds, and mixtures thereof for example HI, lower alkyl iodides, such as methyl iodide, iodoethane, 1-iodobutane, 2-iodobutane, 1,4-diiodobutane, 2-iodopropane, 1-iodopropane and iodoheptane. The most preferred promoter is HI. The promoter and iridium can be present in the same compound, as in iridium iodide. Generally, the concentration of promoter is between 0.05-1.0% by weight based on the weight of the reaction mixture. In addition, the molar ratio of promoter to iridium should be in the range of 0.5:1 to 20:1, preferably 2:1 to 15:1. At molar ratios greater than 20:1, the amount of adipic acid recovered is greatly diminished.

The term "active iodide" means iodide exclusive of that tied up as organoiodides. Iodide compounds such as HI when added to a mixture to be isomerized, form wide variety of other organoiodides which exist in the reaction mixture in equilibrium with HI. The iodide in the organoiodides are not active promoters for the catalyst, but during the course of the isomerization reaction iodide is constantly shifting from the inactive form to the active form and vice versa.

The lactones which are starting materials for this process are liquids at room temperature, and so the use of additional solvent is not essential. However, higher adipic acid yields and conversions are obtained in carboxylic acid solvents. The preferred solvents are acetic acid, valeric acid, and mixtures of carboxylic acids, such as those produced during the hydrocarboxylation of butadiene. Other suitable solvents are those which are stable under the highly acidic, high temperature conditions of the reaction. Other suitable solvents include saturated chlorinated solvents such as methylene chloride; carboxylic acids having 2-10 carbon atoms; aliphatic and aromatic compounds such as toluene, xylene heptane and chlorobenzene; and polar aprotic solvents such as tetramethylene sulfone. If a solvent is used, it will usually be present in about 10 to about 90 percent by weight of the reaction mixture.

Rate increases with decreasing pressure and increasing temperature. Yield increases with increasing pressure and decreasing temperature as long as the product desired is adipic acid (higher pressure operation) and decreases very rapidly under 200–300 psi. Yield is also increased, however, when the pressure is kept very low so that 3-pentenoic acid can be recovered from the mixture as it is formed. Catalyst stability is best at lower temperatures and lower pressures. The usual temperature range useful in the isomerization reaction is about 190 degrees C. to about 250 degrees C. and the CO absolute pressure range is 100 to 2000 psi at the temperature of the reaction. At lower temperatures the reaction is too slow, and at higher temperatures side-reactions, such as decarboxylation, are significant. The optimum temperatur is between 200 degrees C. and 240 degrees C. The optimum CO absolute pressure will depend on the temperature, higher pressures being required to stabilize the catalyst at high temperatures. At 220 degrees C. to 240 degrees, C., the optimum CO pressure is 200–600 psi.

Although water is necessary for the formation of adipic acid from the lactones, the amount of water present at any given time should be kept low, preferably less than one part per 20 parts of solvent. A stoichiometric amount of water may be added at the beginning of the reaction, but it is preferred that it be added continuously as consumed by the reaction to avoid undesirably high concentrations. The amount of water may exceed the stoichiometric amount, but should not be present in great excess.

Isolation of the adipic acid can be accomplished in any of several standard procedures, including, but not limited to, filtration (when reaction mixture is a non-solvent for the adipic acid), solvent extraction, and chromatography.

When the process of the invention is run under conditions favorable to inter-conversion, i.e. isomerization, that is the conversion of a 6 carbon acid to adipic acid, the compound, or mixture of compounds is heated to a temperature in the range of about 170 degrees to 250 degrees C. in the presence of carbon monoxide at a carbon monoxide pressure of 200 to 10,000 psi.

The isomerization may be carried out in a solvent for the compound being isomerized. Lower aliphatic acids are suitable, and acetic acid is satisfactory. Other solvents that may be used are aliphatic halides such as methylene chloride aromatic solvents such as toluene and xylene, and polar aprotic solvents such a tetramethylene sulfone.

A particularly preferred process involves the isomerization of other C6 acids to adipic acid, for example isomerization of 2-methylglutaric acid or 2-ethylsuccinic acid.

Water is not produced during the isomerization reaction. The water content of the reaction mixture should be maintained at a low level, preferably below 5% by weight. Water can be present in amounts as high as 50% by weight of the reaction mixture, but yields and reaction rates will suffer.

When the process of the invention is practiced in a manner to prepare pentenoic acid it is preferred to operate at a temperature in the range of 190 degrees to 230 degrees C. and at pressures of 40 to 260 mm of mercury. Preferably the water content of the reaction mixture should be less than 1% by weight. It is preferred that the iodide to iridium ratio be in the range of about 2.0 to 2.5. This reaction is preferably carried out without a solvent.

EXAMPLE 1

Isomerization of A Mixture of Dibasic Acids and gamma-valerolactone To Form Adipic Acid A 100 ml zirconium mechanically stirred autoclave was flushed with nitrogen and then with 99 parts carbon monoxide/1 part hydrogen. It was then charged with 82 grams of a slurry containing 8.0 grams (78 mmole) of valeric acid, 8.0 grams (78 mmole) of 2-methylbutyric acid, 8.0 grams (80 mmole) of gamma-valerolactone, 8.0 grams (55 mmole) of 2,3-dimethylsuccinic acid, 16 grams (110 mmole) of 2-ethylsuccinic acid, 32 grams of 2-methylglutaric acid, 0.39 grams of 57% aqueous HI (1.7 mmole HI), 1.25 grams of water (70 mmoles), and 0.23 grams (0.66 mmole) iridium dicarbonyl acetylacetonate. The autoclave was then heated to 210 C. and the autoclave pressure then immediately adjusted to 400 psi. The autoclave was allowed to run for 24.3 hours after which it was sampled. The autoclave heating continued for an additional 92.3 hours. It was then cooled to 50 C, vented, and the product was discharged. The autoclave was washed first with 80 ml of 0.1% HI in acetic acid at 200 C., then with 80 ml of acetone at 20 C., and finally with 80 ml of acetic acid at 20 C. The 2 product samples were esterified by heating in a sealed vial at 90 C. for 1 hour with BF3/methanol esterification catalyst. They were analyzed as the methyl esters by capillary gas chromatography. The product distribution in normalized mole % at 0, 24, and 116 hours is:

| Time (Hours) | 0 | 24 | 116 |
|---|---|---|---|
| Adipic Acid | 0 | 1.9 | 2.3 |
| 2-Methylglutaric Acid | 28.7 | 28.1 | 31.4 |
| 2-Ethylsuccinic Acid | 14.2 | 13.7 | 15.0 |
| 2,3-Dimethylsuccinic Acid | 7.2 | 7.6 | 8.4 |
| gamma-Valerolactone | 10.7 | 5.4 | 4.8 |
| Valeric & 2-Methylbutyric Acid | 39.0 | 41.2 | 35.7 |
| Butane, Butenes, Butadiene | 0 | 0.1 | 0 |
| Butanols, Butanone, Iodobutanes | 0 | 0.4 | 1.2 |

EXAMPLE 2

Isomerization of 2-methylglutaric Acid (MGA) to Adipic Acid

A 100 ml zirconium mechanically stirred autoclave was flushed with nitrogen and then with 99 parts carbon monoxide/1 part hydrogen. It was then charged with 85 grams of an acetic acid solution containing 8.0 grams (55 mmole) 2-methylglutaric acid, 0.29 grams 57% aqueous. HI (1.3 mmole HI), 0.22 grams (0.63 mmole) iridium dicarbonyl acetylacetonate and 1.0 grams water. The autoclave was pressured with 99/1 CO/H2 to 200 psi and then heated to 210 degrees C. the autoclave pressure was then immediately adjusted to 700 psi with 99/1 CO/H2. The reaction was allowed to run for a total of 6 hours with intermediate samples taken after with it was cooled to 50 degrees C., vented and the product was discharged. The autoclave was washed with 80 ml of 0.1% HI in acetic acid at 200 degrees C., and then with 80 ml of acetone at 20 degrees C. and finally with 80 ml of acetic acid at 20 degrees C.

A sample of the product was esterified by heating in a sealed vial at 90 degrees C. for 1 hour with BF3/methanol esterification catalyst. It was analyzed as the methyl esters by capillary gas chromatography. The analysis is shown in the following table. 19% of the 2-methylglutaric acid was converted with a 6.8% yield to adipic acid.

EXAMPLE 3

Example 2 was repeated except that the temperature was increased to 230 degrees C. and the total run time was reduced to 4 hours. Analysis of the product showed 84% Methylglutaric acid (MGA) was converted and 4% adipic acid yield.

EXAMPLE 4

Example 2 was repeated except that the autoclave was charged with 8 grams of 2-ethylsuccinic acid (ESA) (55 mmoles) instead of 8.0 grams of methylglutaric acid. The results show about 7.4% conversion of 2-ethylsuccinic acid and a 1.3% yield of adipic acid.

EXAMPLE 5

Example 2 was repeated except that the autoclave was charged with 8.0 grams of 2,3-dimethylsuccinic acid (DMSA) (55 mmoles) instead of 8.0 grams of MGA and the reaction time was increased to 24 hours. The results show about 18% DMSA conversion and a 0.7% yield of adipic acid.

| Example # | 2 | 3 | 4 | 5 |
|---|---|---|---|---|
| % conversion | 19.3 | 84.0 | 7.4 | 18.3 |
| % Yield to: | | | | |
| Adipic acid | 6.8 | 3.8 | 1.3 | 0.7 |
| MGA | N/A | N/A | 3.0 | 8.5 |
| ESA | 2.3 | 5.4 | N/A | 1.3 |
| DMSA | 0.5 | 1.8 | 0.1 | N/A |
| Lactones | 1.2 | 11 | 0 | 0 |
| pentenoic acids | 2.0 | 4.8 | 1.1 | 1.0 |
| VA* + MBA** | 6.5 | 55 | 1.9 | 6.7 |

*VA = valeric acid
**MBA = 2-methylbutyric acid.

EXAMPLE 6

A no solvent (neat) system:

Gamma-valerolactone was hydrocarboxylated using an iridium/iodide catalyst. The iridium was present in the amount of 695 ppm, and the mole ratio (I/Ir) was 2. The reaction was conducted at 210 C. and 700 psig under carbon monoxide. At the end of 160 minutes, solution contained 11.2% adipic acid and the dibasic acids had a linearity of 79%. Adipic acid and pentenoic acid yields were 66.5% and 26.9%, respectively.

EXAMPLE 7

60 grams of 2-methylglutaric acid was melted in a 100 ml glass flask; 0.174 grams of iridium dicarbonyl acetylacetonate and 0.223 grams of HI (57%) were then added. The temperature was maintained ad 100 degrees C. for 30 minutes. and then raised to 150 degrees C. for 60 minutes while the mixture was agitated under a carbon monoxide atmosphere. The reaction flask was then connected to an ice water cooled condenser. Pressure of the system was then reduced to 60 mm Hg. using a water aspirator: the reactor contents were heated to a temperature of 200 degrees C. Most of the products formed distilled over and condensed in the receiver. Butenes, butadiene and carbon monoxide were not condensed and were lost into the vacuum system.

In 21 minutes, 23.6% of the methylglutaric acid was converted. The yield of pentenoic acids was 22.4%; combined valeric/methylbutyric acid was 3.6% Butenes yield was 36.9%. Branched olefinic C5 carboxylic acids (2-methyl-2-butenoic acid, 2-methyl-3-butenoic acid, and 2-ethylpropionic acid) was 37%.

We claim

1. A process for the preparation of adipic acid and/or pentenoic acids which comprises (1) forming a reaction mixture containing (a) one or more acids or lactones selected from saturated branched six carbon diacids, saturated five carbon lactones, saturated six carbon diacid anhydrides and branched mono-olefinic five carbon monoacids (b) carbon monoxide, and (c) an iodide promoted iridium catalyst (2) heating said reaction mixture to a temperature in the range of about 175 degrees C. to about 230 degrees C. while under a carbon monoxide pressure of between 0 to 2000 psi absolute and where the ratio of active iodide to iridium in the reaction mixture is 0.5:1 to 20:1, and the iridium content of the reaction mixture is about 100 to 8,000 parts per million by weight of the reaction mixture.

2. The process of claim 1 in which the major product is pentenoic acids and the carbon monoxide pressure is between 0 and 10 psi absolute.

3. The process of claim 1 in which the major product is adipic acid and the carbon monoxide pressure is between 200 and 2000 psi absolute.

4. The process of claim 1 in which the reaction mixture contains gamma-valerolactone, the temperature is in the range of 190 to 230 degrees C. and the ratio of active iodide to iridium is 2:1 to 5:1.

5. The process of claim 4 in which the major product is adipic acid and the carbon monoxide pressure is between 200 and 2000 psi absolute.

6. The process of claim 1 in which the reaction mixture contains at least one saturated 6 carbon diacid selected from the group consisting of 2-methylglutaric acid, 2-ethylsuccinic, and 2,3-dimethylsuccinic, and the temperature is above 170 degrees C.

7. The process of claim 1 in which water is present the reaction mixture in an amount of below 5% by weight.

* * * * *